United States Patent
Iwasaki

(10) Patent No.: US 11,490,515 B2
(45) Date of Patent: Nov. 1, 2022

(54) EXTENSIBLE AND CONTRACTIBLE WIRING BOARD

(71) Applicant: Murata Manufacturing Co., Ltd., Nagaokakyo (JP)

(72) Inventor: Kazuki Iwasaki, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 0 days.

(21) Appl. No.: 17/215,595

(22) Filed: Mar. 29, 2021

(65) Prior Publication Data

US 2021/0307168 A1    Sep. 30, 2021

Related U.S. Application Data

(63) Continuation of application No. PCT/JP2019/026973, filed on Jul. 8, 2019.

(30) Foreign Application Priority Data

Nov. 2, 2018  (JP) .............................. JP2018-207202

(51) Int. Cl.
    *H05K 1/14*      (2006.01)
    *H05K 1/02*      (2006.01)
    *H01R 12/79*     (2011.01)

(52) U.S. Cl.
    CPC .............. *H05K 1/14* (2013.01); *H05K 1/028* (2013.01); *H05K 1/0218* (2013.01); *H01R 12/79* (2013.01); *H05K 2201/10106* (2013.01)

(58) Field of Classification Search
    CPC ........ H05K 1/14; H05K 1/0218; H05K 1/028; H05K 2201/10106
    See application file for complete search history.

(56) References Cited

U.S. PATENT DOCUMENTS 9,505,046 B2 *  11/2016  Tanaka .................. B21C 37/155
9,717,141 B1 *   7/2017  Tegg ...................... H05K 1/118
(Continued)

FOREIGN PATENT DOCUMENTS

JP    2002016323 A    1/2002
JP    2006108476 A    4/2006
(Continued)

OTHER PUBLICATIONS

International Search Report issued for PCT/JP2019/026973, dated Sep. 10, 2019.
(Continued)

*Primary Examiner* — Hoa C Nguyen
(74) *Attorney, Agent, or Firm* — ArentFox Schiff LLP

(57) ABSTRACT

An extensible and contractible wiring board includes first and second extensible and contractible wiring substrates formed by respective wiring at extensible and contractible substrates. Each of the first and second extensible and contractible wiring substrates has a first end having functional units and an intermediate wiring portion, with the wiring and the functional units of the first and second extensible and contractible wiring substrates not electrically connected. Moreover, the first and second extensible and contractible wiring substrates are electrically independent extensible and contractible wiring substrates, and the wirings and the functional units do not overlap at the first ends of the first and second extensible and contractible wiring substrates in top view of the extensible and contractible wiring board, and the intermediate wiring portions of the first and second extensible and contractible wiring substrates overlap in top view of the extensible and contractible wiring board.

22 Claims, 12 Drawing Sheets

(56) References Cited

U.S. PATENT DOCUMENTS

| | | |
|---|---|---|
| 2002/0135993 A1 | 9/2002 | Ueyama et al. |
| 2009/0188716 A1* | 7/2009 | Nagase .................. H01Q 21/06 174/72 A |
| 2010/0294556 A1* | 11/2010 | Chuo ..................... H05K 1/028 174/268 |
| 2011/0237921 A1 | 9/2011 | Askin, III et al. |
| 2013/0303873 A1 | 11/2013 | Vörös et al. |
| 2018/0077794 A1 | 3/2018 | Iwase |
| 2019/0166713 A1* | 5/2019 | Chen .................. H01R 12/7076 |

FOREIGN PATENT DOCUMENTS

| | | |
|---|---|---|
| JP | 2012253160 A | 12/2012 |
| JP | 2016106735 A | 6/2016 |
| JP | 2017022173 A | 1/2017 |
| JP | 2017183328 A | 10/2017 |
| JP | 2018046160 A | 3/2018 |

OTHER PUBLICATIONS

Written Opinion of the International Searching Authority issued for PCT/JP2019/026973, dated Sep. 10, 2019.

\* cited by examiner

EXTENSIBLE AND CONTRACTIBLE WIRING BOARD

CROSS REFERENCE TO RELATED APPLICATIONS

The present application is a continuation of PCT/JP2019/026973 filed Jul. 8, 2019, which claims priority to JP Application No. 2018-207202, filed Nov. 2, 2018, the entire contents of each of which are incorporated herein by reference.

TECHNICAL FIELD

The present invention relates to an extensible and contractible wiring board.

BACKGROUND ART

In recent years, a state of a human body and the like have been managed by acquiring and analyzing biological information.

For example, an extensible and contractible wiring board in which an extensible and contractible substrate is attached to a living body and used has been known as described in Japanese Patent Application Laid-Open No. 2018-46160 (hereinafter "Patent Document 1").

In the extensible and contractible wiring board illustrated in Patent Document 1, extensible and contractible electrodes and wirings connected to the extensible and contractible electrode have a one-to-one correspondence. A plurality of combinations of the extensible and contractible electrodes and the wirings is provided at the extensible and contractible wiring board. Moreover, the extensible and contractible electrodes are arranged so as not to overlap at one end of the extensible and contractible wiring board. As the extensible and contractible electrodes spread out so as not to overlap, the wirings are also branched and arranged so as not to overlap, for example, as shown in FIG. 1 of Patent Document 1.

In the extensible and contractible wiring board, noises are easily caused at the wirings due to extension and contraction.

In the extensible and contractible wiring board in Patent Document 1, since degrees of extension and contraction applied to the plurality of provided wirings are different, different noises are caused at the plurality of provided wirings.

When different noises are caused at the plurality of provided wiring, since signals are obtained by adding the different noises to signals obtained by the extensible and contractible electrodes, it is difficult to remove the noises by a differential amplifier circuit in the subsequent stage. Thus, there is a problem to reliably obtain measured values.

SUMMARY OF THE INVENTION

Accordingly, the exemplary embodiments of the present invention have been made to solve the above problems. Thus, it is an object of the present invention to provide an extensible and contractible wiring board having a small difference between noises caused at a plurality of the wirings.

In an exemplary aspect, an extensible and contractible wiring board is provided that includes at least a first extensible and contractible wiring substrate formed by forming a wiring at an extensible and contractible substrate and a second extensible and contractible wiring substrate formed by forming a wiring at an extensible and contractible substrate. Each of the first and second extensible and contractible wiring substrates have a first end having functional units and an intermediate wiring portion, with the wiring and the functional units of the first extensible and contractible wiring substrate and the wiring and the functional units of the second extensible and contractible wiring substrate are not electrically connected. Moreover, the first and second extensible and contractible wiring substrates are electrically independent extensible and contractible wiring substrates. The wirings and the functional units do not overlap at the first ends of the first extensible and contractible wiring substrate and the second extensible and contractible wiring substrate in top view of the extensible and contractible board. Furthermore, the intermediate wiring portions of the first extensible and contractible wiring substrate and the second extensible and contractible wiring substrate overlap in top view of the extensible and contractible wiring board.

Another exemplary aspect of the extensible and contractible wiring board includes at least a first extensible and contractible wiring substrate formed by forming a wiring at an extensible and contractible substrate and a second extensible and contractible wiring substrate formed by forming a wiring at an extensible and contractible substrate. Each of the first and second extensible and contractible wiring substrates has a first end having a wiring and an intermediate wiring portion. Moreover, the wiring of the first extensible and contractible wiring substrate and the wiring of the second extensible and contractible wiring substrate are not electrically connected. The first extensible and contractible wiring substrate and the second extensible and contractible wiring substrate are electrically independent extensible and contractible wiring substrates. The wirings do not overlap at the first ends of the first extensible and contractible wiring substrate and the second extensible and contractible wiring substrate in a top view of the extensible and contractible wiring board. Furthermore, the intermediate wiring portions of the first extensible and contractible wiring substrate and the second extensible and contractible wiring substrate overlap in top view of the extensible and contractible wiring board.

According to the present invention, an extensible and contractible wiring board is provided that has a small difference with a small difference between noises caused at a plurality of provided wirings.

DETAILED DESCRIPTION

Hereinafter, exemplary embodiments of an extensible and contractible wiring board will be described.

However, it is noted that the exemplary embodiments of the present invention are not limited to the following configurations, and that they can be appropriately changed and applied without departing from the gist of the invention. Moreover, it is noted that a combination of two or more individual desirable configurations of the exemplary embodiments described below are also the present invention.

Needless to say, the exemplary embodiments to be illustrated below are examples, and partial configurations illustrated in different embodiments can be replaced or combined. In second and subsequent embodiments, matters common to a first embodiment will not be described, and only different points will be described. In particular, similar actions and effects due to similar configurations will not be mentioned sequentially for each embodiment.

First Exemplary Embodiment

Although the extensible and contractible wiring board of the exemplary embodiments includes at least two extensible and contractible wiring substrates (e.g., a first extensible and contractible wiring substrate and a second extensible and contractible wiring substrate), an example in which the extensible and contractible wiring board includes three extensible and contractible wiring substrates is illustrated in each embodiment of the extensible and contractible wiring board to be illustrated below.

Each extensible and contractible wiring substrate including the extensible and contractible wiring board may have a first end portion (or simply a first end) and an intermediate wiring portion (or simply an intermediate wiring), and it is not an essential requirement for each extensible and contractible wiring substrate to have a second end portion. However, an example in which the extensible and contractible wiring substrate has the second end portion (or simply a second end) is illustrated in each exemplary embodiment to be described below.

Figure 1:
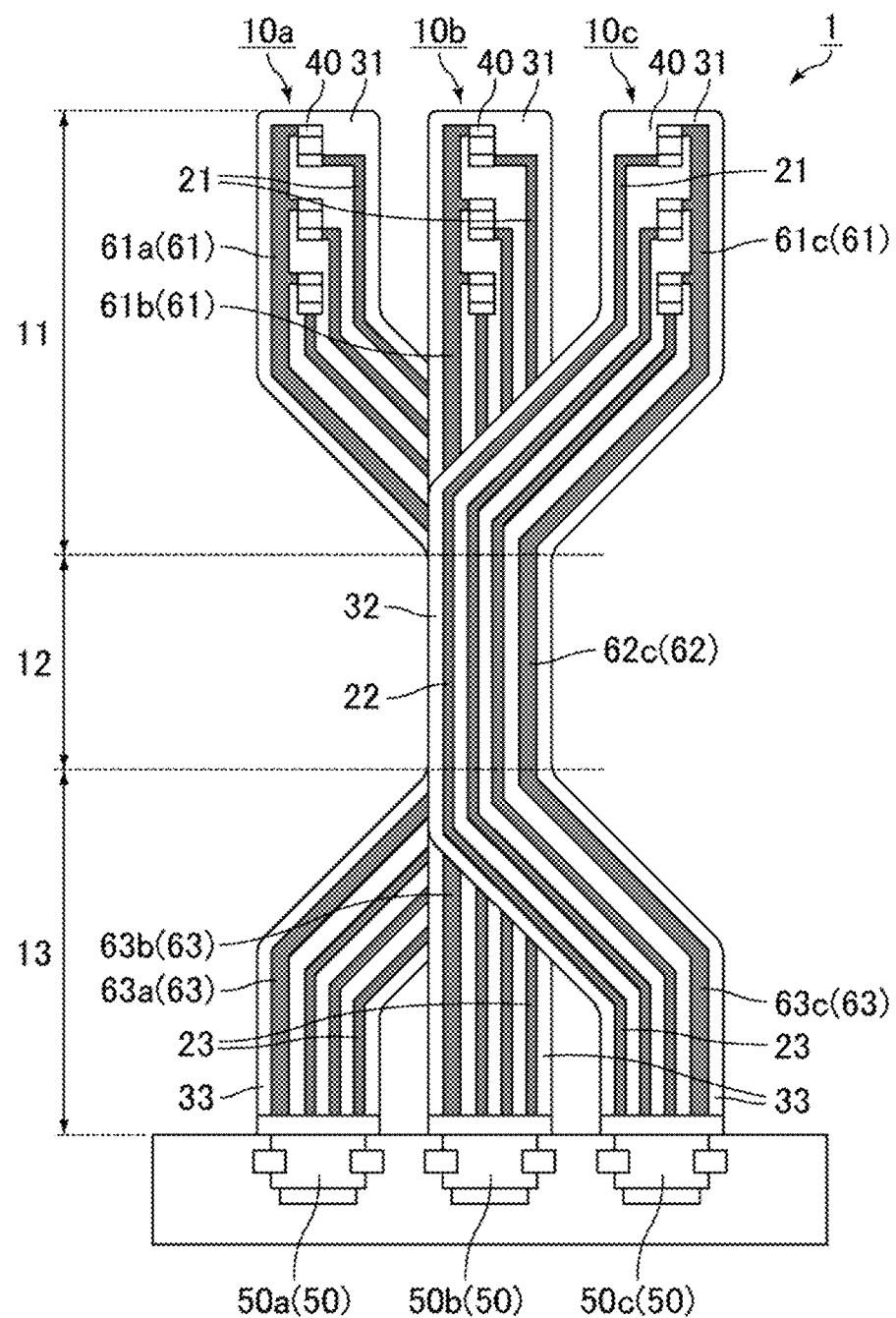
FIG. 1 is a top view schematically illustrating an extensible and contractible wiring board according to a first exemplary embodiment.

FIG. 1 is a top view schematically illustrating an extensible and contractible wiring board according to a first exemplary embodiment.

Figure 2:
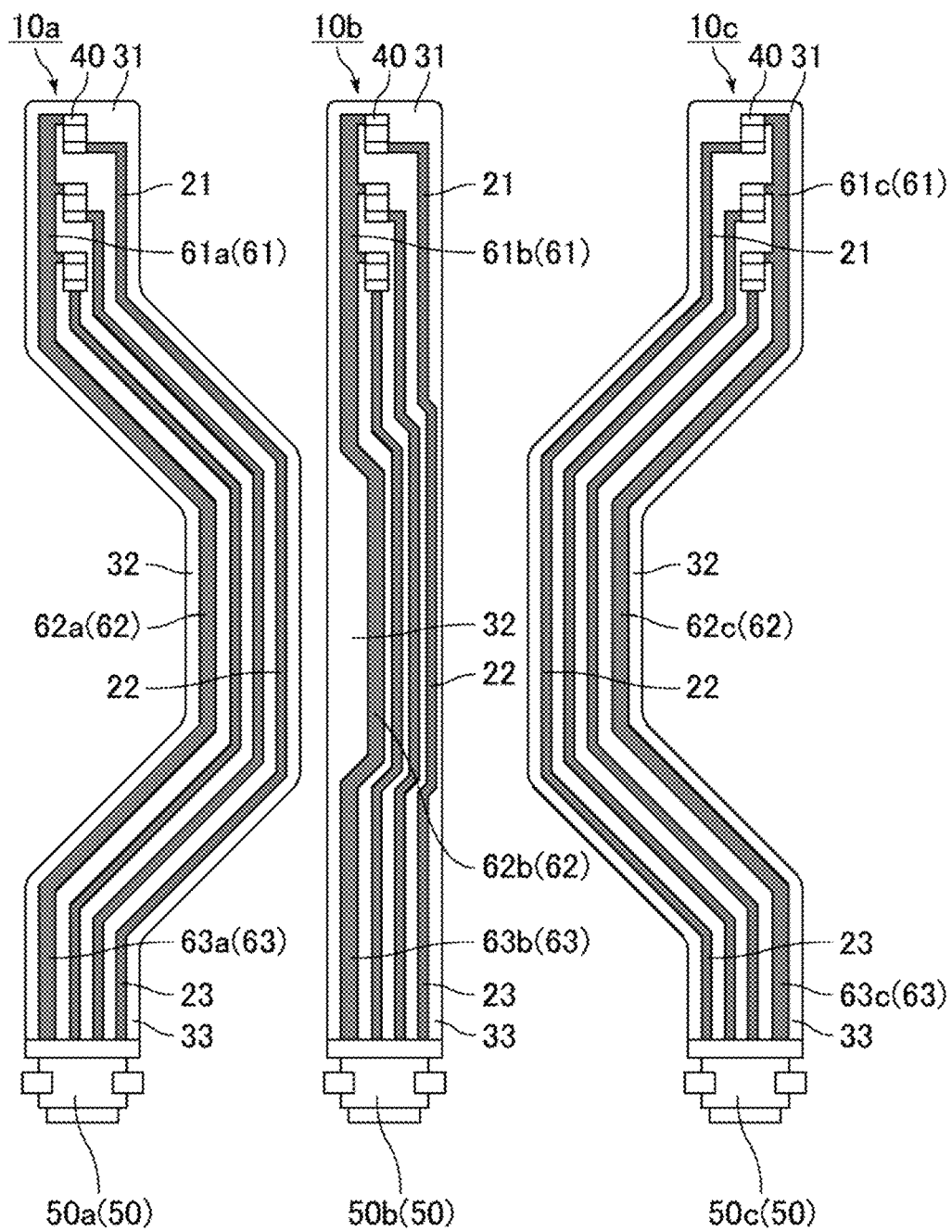
FIG. 2 is a top view schematically illustrating extensible and contractible wiring substrates constituting the extensible and contractible wiring board according to the first exemplary embodiment.

FIG. 2 is a top view schematically illustrating extensible and contractible wiring substrates constituting the extensible and contractible wiring board according to the first exemplary embodiment.

An extensible and contractible wiring board 1 illustrated in FIG. 1 includes a first extensible and contractible wiring substrate 10*a*, a second extensible and contractible wiring substrate 10*b*, and a third extensible and contractible wiring substrate 10*c*.

Each extensible and contractible wiring substrate is formed by forming wirings (indicated by reference symbols 21, 22, and 23) at extensible and contractible substrates (indicated by reference symbols 31, 32, and 33).

Each extensible and contractible wiring substrate has a first end 11, an intermediate wiring 12, and a second end 13 of which ranges are generally indicated by two-way arrows, respectively.

The first extensible and contractible wiring substrate 10*a*, the second extensible and contractible wiring substrate 10*b*, and the third extensible and contractible wiring substrate 10*c* are extensible and contractible wiring substrates independent from each other as illustrated in FIG. 2, and are electrically not connected. The extensible and contractible wiring board 1 illustrated in FIG. 1 is formed by stacking the first extensible and contractible wiring substrate 10*a* as a lowermost (or bottom) layer, the second extensible and contractible wiring substrate 10*b* as an intermediate (or middle) layer, and the third extensible and contractible wiring substrate 10*c* as an uppermost (or top) layer.

The extensible and contractible substrate in the extensible and contractible wiring board can be made of, for example, an extensible and contractible resin material. Examples of the resin material for forming the extensible and contractible substrate include thermoplastic polyurethane and the like.

When the extensible and contractible substrate is the resin material, the extensible and contractible substrates can be bonded to each other at the intermediate wiring portion 12 by stacking the plurality of extensible and contractible wiring substrates and thermally pressure-bonding the extensible and contractible wiring substrates. A positional relationship between the plurality of extensible and contractible wiring substrates can be fixed at the intermediate wiring portion.

In order to thermally pressure-bond the extensible and contractible substrates to each other, the resin material is preferably a thermoplastic resin.

When the extensible and contractible substrates are not thermally pressure-bonded to each other, the positional relationship may be fixed by bonding the extensible and contractible wiring substrates to each other with an adhesive.

The wirings in the extensible and contractible wiring board are made of, for example, a mixture of a metal powder such as Ag or Cu and an elastomer resin such as a silicone resin.

Although the extensible and contractible wiring substrate is formed by forming the wiring at the extensible and contractible substrate, the extensible and contractible substrates at the first end 11, the intermediate wiring 12, and the second end 13 are illustrated as the extensible and contractible substrate 31, the extensible and contractible substrate 32, and the extensible and contractible substrate 33, respectively, and the wirings at the first end 11, the intermediate wiring 12, and the second end 13 are illustrated as the wiring 21, the wiring 22, and the wiring 23, respectively.

It is preferable that the first end 11, the intermediate wiring 12, and the second end 13 are integrated as a continuous member. That is, it is preferable that the extensible and contractible substrate 31, the extensible and contractible substrate 32, and the extensible and contractible substrate 33 forming the first end 11, the intermediate wiring 12, and the second end 13 are a continuous member. It is preferable that the wiring 21, the wiring 22, and the wiring 23 forming the first end 11, the intermediate wiring 12, and the second end 13 are a continuous wiring. When the wiring 21, the wiring 22, and the wiring 23 are the continuous wiring, connection terminals and the like are not provided between the wiring 21, the wiring 22, and the wiring 23.

A functional unit 40 is connected to the wiring 21 at the first end 11 of each of the first extensible and contractible wiring substrate 10a, the second extensible and contractible wiring substrate 10b, and the third extensible and contractible wiring substrate 10c.

An LED element, which can be a heating element, is illustrated as the functional unit 40 in the extensible and contractible wiring board 1.

The first end 11 is a portion at which the functional units connected to the wirings are provided. Examples of the functional unit include heating elements (LED elements, semiconductor parts, passive parts (LCR parts and the like), antennas, circuit modules, actuators (motors, piezoelectric elements, speakers, and the like), displays, batteries, relays, heaters, and the like), sensors (electrodes, chip sensors such as thermistors, acceleration sensors, and optical system sensors, semiconductor parts, antennas, circuit modules, chemical sensors, strain sensors, capacitance detection sensors, force sensors, microphones, actuators (motors, piezoelectric elements, speakers, and the like), and imaging elements), and the like. Examples of the functional unit other than the heating elements and the sensors include connectors, switches, and the like.

The wiring 21 and the functional unit 40 at the first end 11 do not overlap in top view of the extensible and contractible wiring board 1. That is, the functional units spread out so as not to overlap in top view of the extensible and contractible wiring board.

The intermediate wiring 12 includes the wiring 22.

The intermediate wiring portions 12 of the first extensible and contractible wiring substrate 10a, the second extensible and contractible wiring substrate 10b, and the third extensible and contractible wiring substrate 10c overlap in top view of the extensible and contractible wiring board 1.

The extensible and contractible wiring board 1 has the second end 13 that is an end portion opposite to the first end 11.

The second end 13 includes the wiring 23.

A connector 50a, a connector 50b, and a connector 50c are connected to ends of the wirings 23 at the second end 13 of the first extensible and contractible wiring substrate 10a, the second extensible and contractible wiring substrate 10b, and the third extensible and contractible wiring substrate 10c.

The second end portions 13 of the first extensible and contractible wiring substrate 10a, the second extensible and contractible wiring substrate 10b, and the third extensible and contractible wiring substrate 10c do not overlap in top view of the extensible and contractible wiring board 1.

The wirings 23 at the second ends 13 spread out so as not to overlap in top view of the extensible and contractible wiring board 1, and the wirings are individually connected to the connectors 50.

In the extensible and contractible wiring board of the exemplary embodiment, the intermediate wiring portions of the extensible and contractible wiring substrates overlap in top view of the extensible and contractible wiring board. Accordingly, it is possible to obtain an extensible and contractible wiring board with a small difference between noises at a plurality of provided wirings.

The reason why this effect is exhibited will be described with reference to the drawings.

Figure 3A:
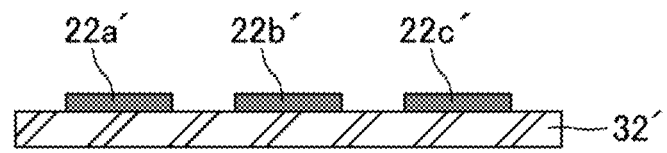
FIGS. 3A and 3B are sectional views schematically illustrating influences of extension and contraction when intermediate wiring portions of the extensible and contractible wiring substrates do not overlap in top view of the extensible and contractible wiring board.
Figure 3B:
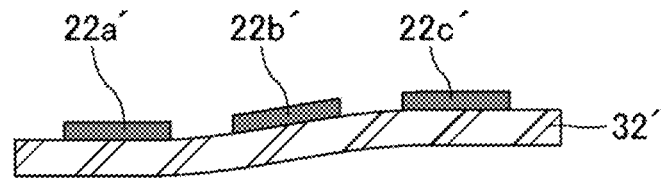

FIGS. 3A and 3B are sectional views schematically illustrating influences of extension and contraction when the intermediate wiring portions of the extensible and contractible wiring substrates do not overlap in top view of the extensible and contractible wiring board.

Figure 4A:
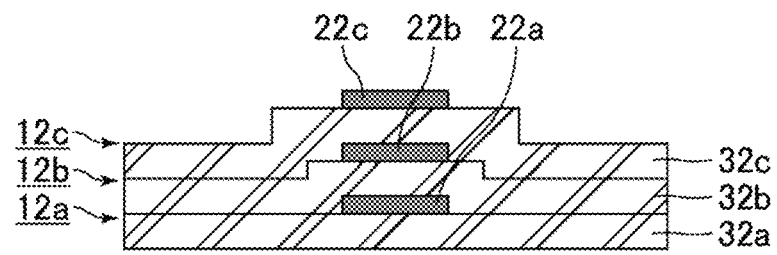
FIGS. 4A and 4B are sectional views schematically illustrating influences of extension and contraction when the intermediate wiring portions of the extensible and contractible wiring substrates overlap in top view of the extensible and contractible wiring board.
Figure 4B:
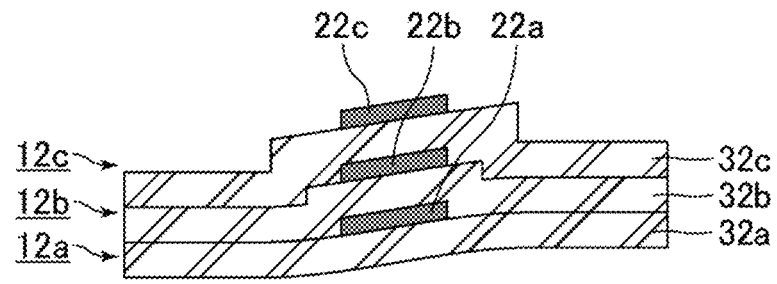

FIGS. 4A and 4B are sectional views schematically illustrating influences of extension and contraction when the intermediate wiring portions of the extensible and contractible wiring substrates overlap in top view of the extensible and contractible wiring board.

In FIG. 3A, a case where a wiring 22a', a wiring 22b', and a wiring 22c' of the intermediate wiring portion of the extensible and contractible wiring substrate are arranged in the same plane without overlapping in top view of the extensible and contractible wiring board is illustrated. FIG. 3B illustrates a scene of a case where the extensible and contractible substrate of such an extensible and contractible wiring substrate extends and contracts.

As illustrated in FIG. 3B, when an extensible and contractible substrate 32' extends and contracts, degrees of extension and contraction (i.e., directions and extension and contraction amounts) applied to the wiring 22a', the wiring 22b', and the wiring 22c' are different between the wirings.

Thus, different noises are caused for the wiring 22a', the wiring 22b', and the wiring 22c'.

In FIG. 4A, a case where the wiring 22a, the wiring 22b, and the wiring 22c at the intermediate wiring portion 12a, the intermediate wiring portion 12b, and the intermediate wiring portion 12c of the first extensible and contractible wiring substrate 10a, the second extensible and contractible wiring substrate 10b, and the third extensible and contractible wiring substrate 10c overlap in top view of the extensible and contractible wiring board is illustrated. FIG. 4B illustrates a scene of a case where the extensible and contractible substrates of such extensible and contractible wiring substrates extend and contract.

As illustrated in FIG. 4B, when the extensible and contractible substrate 32a, the extensible and contractible substrate 32b, and the extensible and contractible substrate 32c of the intermediate wiring portion 12a, the intermediate wiring portion 12b, and the intermediate wiring portion 12c extend and contract, degrees of extension and contraction (i.e., directions and extension and contraction amounts) applied to the wiring 22a, the wiring 22b, and the wiring 22c are the same between the wirings.

Thus, degrees of noises caused at the wiring 22a, the wiring 22b, and the wiring 22c are approximately equal as well.

For this reason, the extensible and contractible wiring board of the exemplary embodiment can be an extensible and contractible wiring board with a small difference between noises at a plurality of provided wirings.

In the extensible and contractible wiring board of the present invention, in each of the first extensible and contractible wiring substrate and the second extensible and contractible wiring substrate, it is preferable that the functional units are the heating elements and the ground wirings that are connected to the heating elements and are formed at the first end, the intermediate wiring, and the second end are provided.

It is preferable that the ground wirings formed at the intermediate wiring portions of the first extensible and contractible wiring substrate and the second extensible and contractible wiring substrate do not overlap in top view of the extensible and contractible wiring board.

It is preferable that the heating elements are the LED elements and the connectors that are provided at the second end and electrically connected to a conversion board that controls supply of power to the LED elements are provided.

Hereinafter, the exemplary embodiments of the extensible and contractible wiring board including the heating elements, the ground wirings, and the connectors will be described.

In the extensible and contractible wiring board 1 illustrated in FIG. 1, the functional unit 40 at the first end 11 of each extensible and contractible wiring substrate is a heating element 40. One terminal of the heating element 40 is connected to the wiring 21, and the other terminal is connected to a ground wiring 61. The ground wiring 61 is a wiring in which the wirings from the heating elements 40 are integrated into one wiring, and is a wiring which is thicker than the wiring 21, and through which a large current flows.

The ground wiring 61 extends to the intermediate wiring 12 and the second end 13 and is connected to the connector 50. The ground wirings at the intermediate wiring 12 and the second end 13 are illustrated as a ground wiring 62 and a ground wiring 63, respectively.

The ground wiring is provided on each extensible and contractible wiring substrate. As illustrated in FIG. 2, the ground wirings are provided at the first extensible and contractible wiring substrate 10a, the second extensible and contractible wiring substrate 10b, and the third extensible and contractible wiring substrate 10c.

The ground wirings at the first ends 11 of the first extensible and contractible wiring substrate 10a, the second extensible and contractible wiring substrate 10b, and the third extensible and contractible wiring substrate 10c are indicated by reference symbols 61a, 61b, and 61c, respectively, the ground wirings at the intermediate wirings 12 are indicated by reference symbols 62a, 62b, and 62c, respectively, and the ground wirings at the second ends 13 are indicated by reference symbols 63a, 63b, and 63c, respectively.

In the extensible and contractible wiring substrate of the related art, since the wirings from all the heating elements are integrated into one ground wiring, current flowing through the ground wiring is large and the heat generation is increased.

On the other hand, in the extensible and contractible wiring board of the present embodiment, since the ground wirings are provided at the extensible and contractible wiring substrates, current flowing per ground wiring is decreased, and heat generation at the ground wiring can be reduced.

In the extensible and contractible wiring board of the present embodiment, the ground wiring 62a, the ground wiring 62b, and the ground wiring 62c formed at the intermediate wirings 12 of the first extensible and contractible wiring substrate 10a, the second extensible and contractible wiring substrate 10b, and the third extensible and contractible wiring substrate 10c do not overlap in top view of the extensible and contractible wiring board.

In top view of the intermediate wiring 12 of the extensible and contractible wiring board 1, the ground wiring 62a, the ground wiring 62b, and the ground wiring 62c are arranged on a left side, a center, and a right side so as to extend in parallel.

As described above, when the ground wirings formed at the intermediate wiring portions of the extensible and contractible wiring substrates do not overlap in top view of the extensible and contractible wiring board, heat generated at the ground wirings is efficiently dissipated.

The connectors 50 are connected to the wirings 23 at the second ends 13 of the extensible and contractible wiring substrates and are also connected to the ground wirings 63.

The connectors 50 are a plurality of small pin connectors corresponding to each of the first extensible and contractible wiring substrate 10a, the second extensible and contractible wiring substrate 10b, and the third extensible and contractible wiring substrate 10c, and can be the connector 50a, the connector 50b, and the connector 50c.

It is preferable that the conversion board that controls the supply of the power to the plurality of heating elements (e.g., LED elements) can be electrically connected to tips of the connectors.

It is preferable that the extensible and contractible wiring board of the present embodiment is used for a visual function monitoring device. Specifically, it is preferable that the extensible and contractible wiring board is used as a photic stimulation pad (hereinafter, referred to as a "VEP pad") for improving evaluation accuracy of a visual evoked potential (hereinafter, referred to as a "VEP"), which is one of intraoperative monitoring in a neurosurgery procedure.

It is noted that the VEP is an abbreviation for visual evoked potential.

The visual function monitoring device that enables various controls, such as a light emission period and light emission intensity of each LED, can be provided and the visual function monitoring device that enables position identification of a pupil by mounting a light intensity adjustment mechanism for each LED element on the conversion board connected to the tip of the connector.

In the extensible and contractible wiring board of the present invention, it is preferable that the wirings of the intermediate wiring portions of the first extensible and contractible wiring substrate and the second extensible and contractible wiring substrate overlap in top view of the extensible and contractible wiring board.

When the wirings of the intermediate wiring portions of the extensible and contractible wiring substrates overlap in top view of the extensible and contractible wiring board, since the degrees of extension and contraction applied to the wirings at the intermediate wiring portions further match each other, an extensible and contractible wiring board with a smaller difference between the noises caused at the plurality of provided wirings can be achieved.

It is also noted that in the extensible and contractible wiring board of the exemplary embodiment illustrated in FIG. 1, the wirings of the intermediate wiring portions in the extensible and contractible wiring substrates do not totally overlap in top view of the extensible and contractible wiring board. However, a positional relationship with the ground wiring is changed, and thus, the wirings of the intermediate wiring portions in the extensible and contractible wiring substrates can be designed so as to overlap in top view of the extensible and contractible wiring board.

Second Exemplary Embodiment

Next, another embodiment of the extensible and contractible wiring board of the present invention will be described.

In the extensible and contractible wiring board of the present invention, the functional unit may be a sensor, and the ground wiring may not be provided. Hereinafter, an exemplary embodiment of such an extensible and contractible wiring board will be described.

Figure 5:
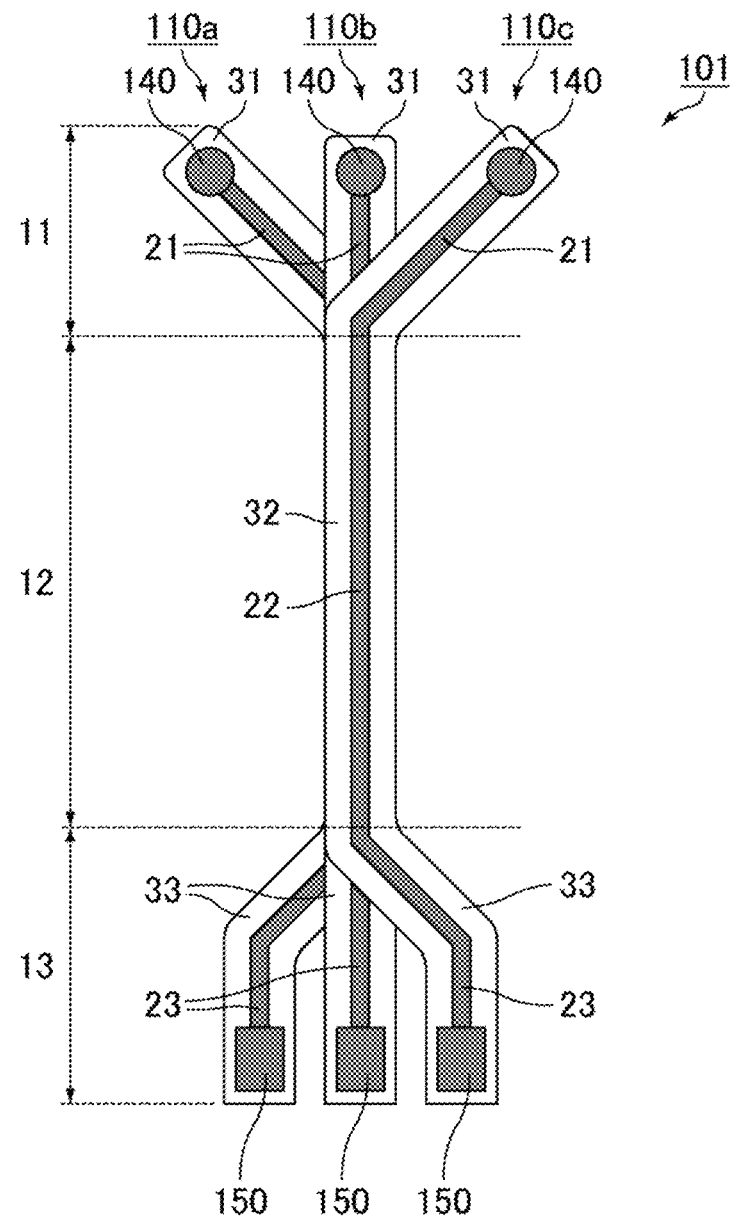
FIG. 5 is a top view schematically illustrating an extensible and contractible wiring board according to a second exemplary embodiment.
Figure 6:
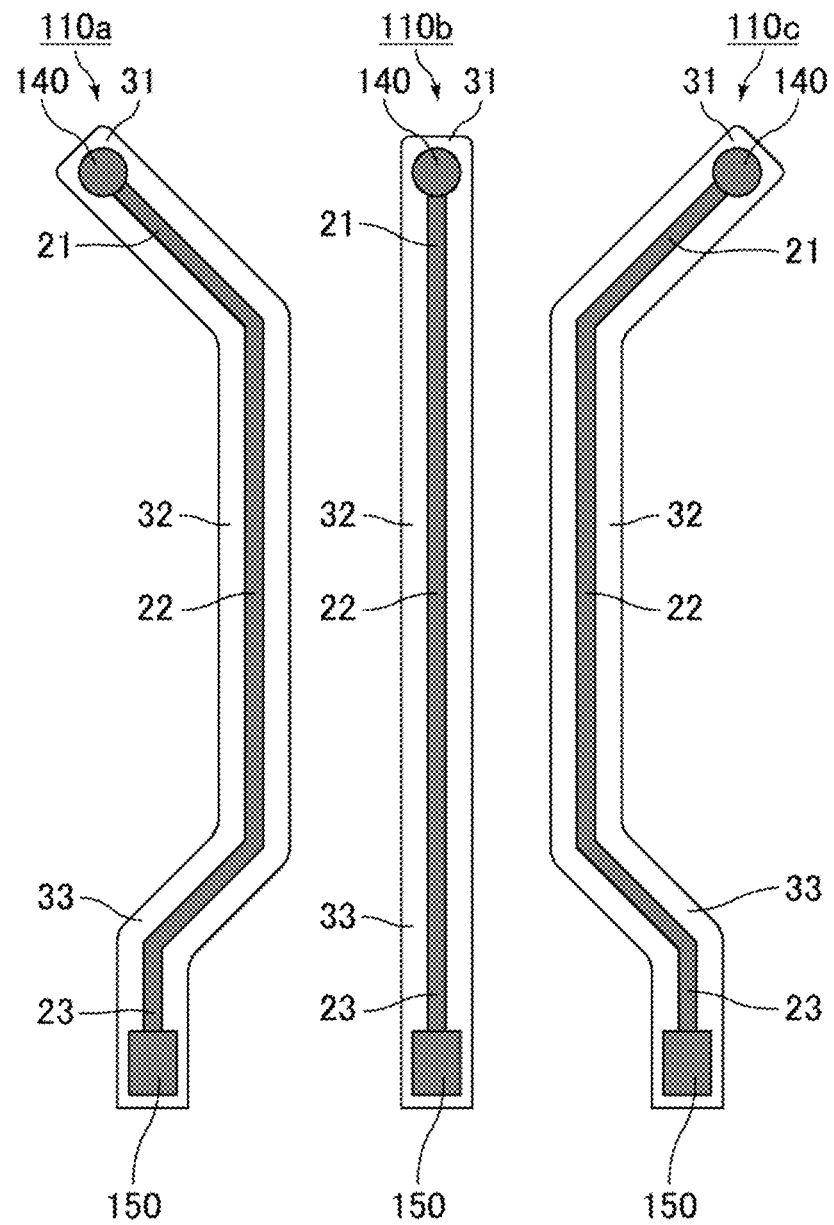
FIG. 6 is a top view schematically illustrating extensible and contractible wiring substrates constituting the extensible and contractible wiring board according to the second exemplary embodiment.

FIG. 5 is a top view schematically illustrating an extensible and contractible wiring board according to a second exemplary embodiment. FIG. 6 is a top view schematically illustrating extensible and contractible wiring substrates constituting the extensible and contractible wiring board according to the second exemplary embodiment.

As shown, an extensible and contractible wiring board 101 illustrated in FIG. 5 includes a first extensible and contractible wiring substrate 110a, a second extensible and contractible wiring substrate 110b, and a third extensible and contractible wiring substrate 110c.

Each extensible and contractible wiring substrate is formed by forming wirings (indicated by reference symbols 21, 22, and 23) at extensible and contractible substrates (indicated by reference symbols 31, 32, and 33).

Each extensible and contractible wiring substrate has a first end 11, an intermediate wiring 12, and a second end 13 of which ranges are indicated by two-way arrows, respectively.

The first extensible and contractible wiring substrate 110a, the second extensible and contractible wiring substrate 110b, and the third extensible and contractible wiring substrate 110c are independent extensible and contractible wiring substrates as illustrated in FIG. 6, respectively, and are not electrically connected. The extensible and contractible wiring board 101 illustrated in FIG. 5 is formed by stacking the first extensible and contractible wiring substrate 110a as a lowermost layer, the second extensible and contractible wiring substrate 110b as an intermediate layer, and the third extensible and contractible wiring substrate 110c as an uppermost layer.

A sensor (e.g., sensor electrode) is illustrated as a functional unit 140 in the extensible and contractible wiring board 101.

The wirings 21 and the functional units 140 at the first ends 11 do not overlap in top view of the extensible and contractible wiring board 101. That is, the functional units spread out so as not to overlap in top view of the extensible and contractible wiring board.

When the functional unit 140 is the sensor, the functional unit may be a wiring pattern (for example, a comb-tooth type wiring pattern) instead of the sensor electrode.

The intermediate wiring portion 12 includes the wiring 22.

The intermediate wiring portions 12 (or simply intermediate wirings) of the first extensible and contractible wiring substrate 110a, the second extensible and contractible wiring substrate 110b, and the third extensible and contractible wiring substrate 110c overlap in top view of the extensible and contractible wiring board 101.

The wirings 22 of the intermediate wiring portions 12 in the extensible and contractible wiring substrates overlap in top view of the extensible and contractible wiring board. Thus, since the degrees of extension and contraction applied to the wirings 22 in the intermediate wirings 12 further match each other, an extensible and contractible wiring board with a smaller difference between noises caused at the plurality of provided wirings 22 can be achieved.

The extensible and contractible wiring board 101 has the second end 13 which is an end portion opposite to the first end 11.

The second end 13 includes the wiring 23.

Connectors 150 are connected to ends of the wirings 23 at the second end 13 of the first extensible and contractible wiring substrate 110a, the second extensible and contractible wiring substrate 110b, and the third extensible and contractible wiring substrate 110c. The connector 150 illustrated herein has a different shape from the shape of the connector 50 illustrated in FIG. 1.

In the present embodiment, the second ends 13 of the first extensible and contractible wiring substrate 110a, the second extensible and contractible wiring substrate 110b, and the third extensible and contractible wiring substrate 110c do not overlap in top view of the extensible and contractible wiring board 101.

The wirings 23 at the second ends 13 spread out so as not to overlap in top view of the extensible and contractible wiring board 101, and the wirings are individually connected to the connectors 150.

When the functional unit provided at the extensible and contractible wiring board is a plurality of sensors, a difference between signals obtained by the plurality of sensors may be used in a differential amplifier circuit provided at a tip of the connector. In this case, the difference between the caused noises for the signals obtained by the sensors are set to be approximately equal, the influence of the noise can be reduced.

The first extensible and contractible wiring substrate 110a and the third extensible and contractible wiring substrate 110c are bent at a boundary between the first end 11 and the intermediate wiring 12 and a boundary between the intermediate wiring 12 and the second end 13. The strength of the bent portion is increased by overlapping and fixing the bent portion which is a portion at which the extensible and contractible wiring substrate is bent.

Third Exemplary Embodiment

Next, still another embodiment of the extensible and contractible wiring board of the present invention will be described. In the extensible and contractible wiring board of the present invention, the extensible and contractible substrate at the first end of the extensible and contractible wiring substrate as the lowermost layer may be positioned under the extensible and contractible substrate and the functional unit of the first end of another extensible and contractible wiring substrate, and the extensible and contractible substrate of the first end of another extensible and contractible wiring substrate may be fixed to the extensible and contractible substrate of the first end of the extensible and contractible wiring substrate as the lowermost layer.

Hereinafter, an exemplary embodiment of such an extensible and contractible wiring board will be described.

A configuration of the extensible and contractible wiring board to be illustrated below is similar to the configuration of the extensible and contractible wiring board of the second embodiment except for the configuration of the first extensible and contractible wiring board which is the extensible and contractible wiring substrate as the lowermost layer, and thus, portions different from the portions of the extensible and contractible wiring board of the second embodiment will be described.

Figure 7:
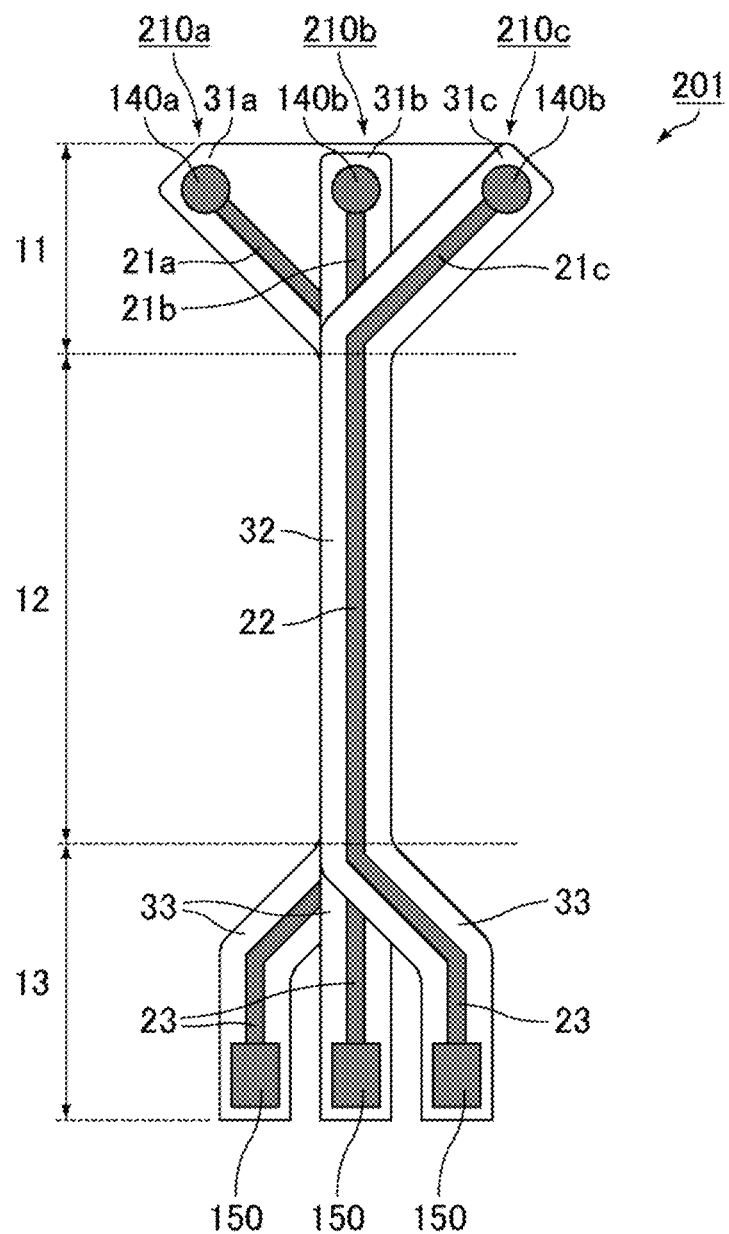
FIG. 7 is a top view schematically illustrating an extensible and contractible wiring board according to a third exemplary embodiment.

FIG. 7 is a top view schematically illustrating an extensible and contractible wiring board according to a third exemplary embodiment.

Figure 8:
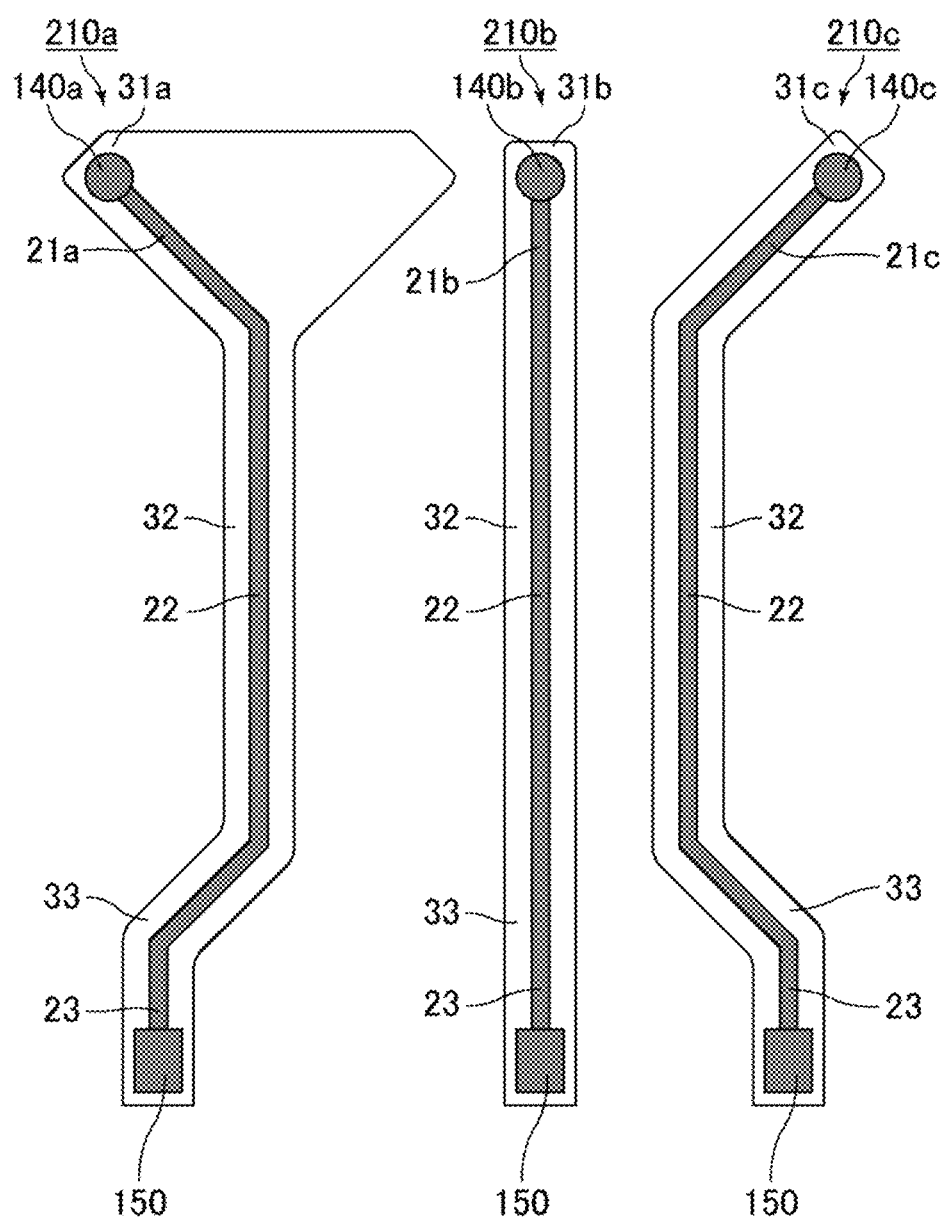
FIG. 8 is a top view schematically illustrating extensible and contractible wiring substrates constituting the extensible and contractible wiring board according to the third exemplary embodiment.

FIG. 8 is a top view schematically illustrating extensible and contractible wiring substrates constituting the extensible and contractible wiring board according to the third exemplary embodiment.

an extensible and contractible wiring board 201 illustrated in FIG. 7 includes a first extensible and contractible wiring substrate 210a, a second extensible and contractible wiring substrate 210b, and a third extensible and contractible wiring substrate 210c.

The first extensible and contractible wiring substrate 210a is an extensible and contractible wiring substrate as a lowermost layer.

A functional unit 140a and a wiring 21a are provided at an extensible and contractible substrate 31a of a first end 11 included in the first extensible and contractible wiring substrate 210a.

The extensible and contractible substrate 31a is wider than a region in which the functional unit 140a and the wiring 21a are provided at the first end 11 of the first extensible and contractible wiring substrate 210a.

The extensible and contractible substrate 31a is positioned under an extensible and contractible substrate 31b, an extensible and contractible substrate 31c, a wiring 21b, a wiring 21c, a functional unit 140b, and a functional unit 140c at the first ends 11 of the second extensible and contractible wiring substrate 210b and the third extensible and contractible wiring substrate 210c.

In the extensible and contractible wiring board 201 of the present embodiment, the extensible and contractible substrate 31a of the first end 11 included in the first extensible and contractible wiring substrate 210a is fixed to the extensible and contractible substrate 31b and the extensible and contractible substrate 31c of the second extensible and contractible wiring substrate 210b and the third extensible and contractible substrate 210c. The extensible and contractible substrates can be fixed to each other by thermally pressure-bonding resin materials of the extensible and contractible substrates.

With such a configuration, since the position where the sensor which is the functional unit is provided is fixed on the same extensible and contractible substrate, relative position accuracy between the sensors is improved. Moreover, detection accuracy can be improved in some sensors.

The ease of attaching the functional unit can be improved at the time of manufacturing.

Fourth Exemplary Embodiment

Next, still another embodiment of the extensible and contractible wiring board of the present invention will be described.

The extensible and contractible wiring board of the present invention further can include a covering material that covers the extensible and contractible wiring board, and an opening corresponding to the position of the functional unit may be provided at the covering material.

Hereinafter, an embodiment of such an extensible and contractible wiring board will be described.

Since a configuration of the extensible and contractible wiring board to be illustrated below is similar to the configuration of the extensible and contractible wiring board of the second embodiment except that the covering material is provided, portions different from the portions of the extensible and contractible wiring board of the second embodiment will be described.

Figure 9:
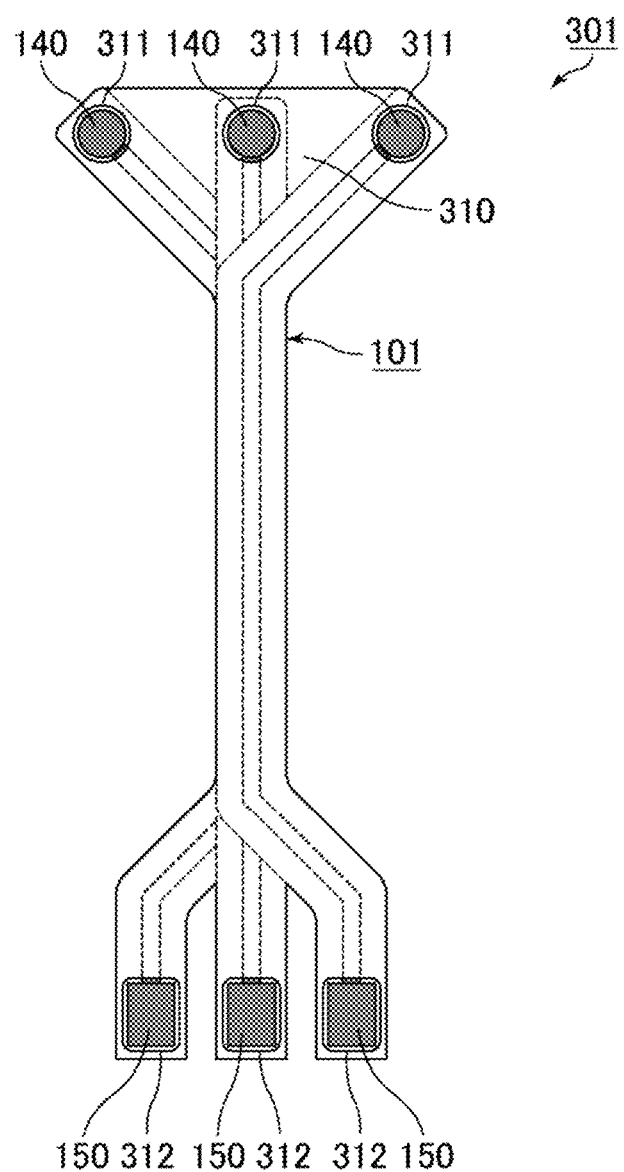
FIG. 9 is a top view schematically illustrating an extensible and contractible wiring board according to a fourth exemplary embodiment.

FIG. 9 is a top view schematically illustrating an extensible and contractible wiring board according to a fourth exemplary embodiment.

Figure 10:
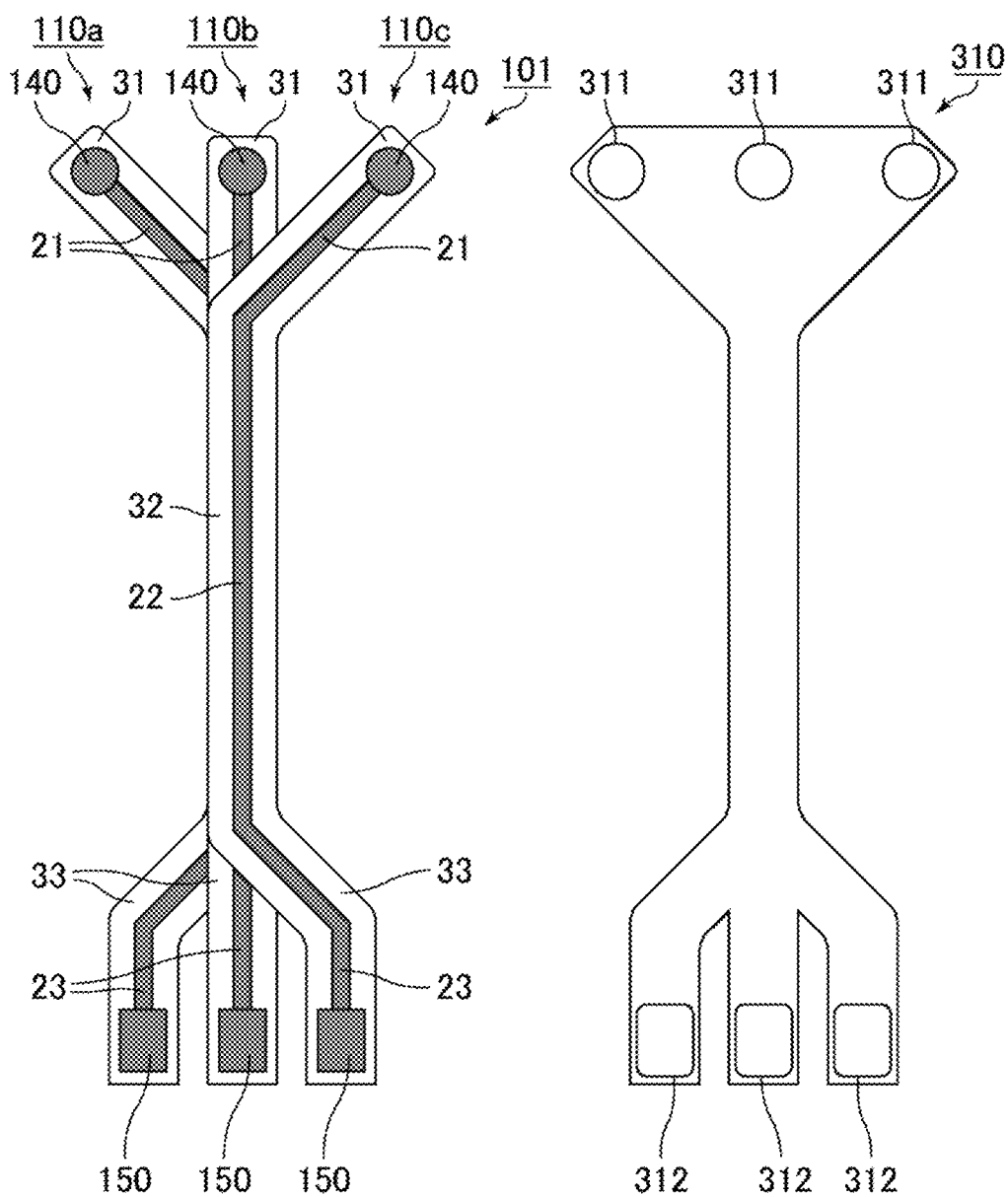
FIG. 10 is a top view schematically illustrating an extensible and contractible wiring board and a covering material including the extensible and contractible wiring board according to the fourth exemplary embodiment.

FIG. 10 is a top view schematically illustrating an extensible and contractible wiring board and a covering material constituting the extensible and contractible wiring board according to the fourth exemplary embodiment.

In an extensible and contractible wiring board 301 illustrated in FIG. 9, the extensible and contractible wiring board 101 of the second exemplary embodiment illustrated in FIG. 5 is covered with a covering material 310.

The extensible and contractible wiring board 101 of the second exemplary embodiment is illustrated on a left side of FIG. 10, and the covering material 310 is illustrated on a right side.

The covering material 310 has openings 311 corresponding to positions of functional units 140.

As further shown, the covering material 310 has openings 312 corresponding to positions of connectors 150.

That is, in the extensible and contractible wiring board 301 of the present embodiment, the functional units 140 and the connectors 150 are exposed from the covering material 310.

Thus, functions of the functional unit 140 and the connector 150 can be exhibited similarly to the functions when the covering material 310 is not provided.

It is noted that in the extensible and contractible wiring board of the present embodiment, the covering material may or may not have the openings corresponding to the positions of the connectors.

Moreover, a material of the covering material is not particularly limited, but may be preferably a resin material similar to the material of the extensible and contractible substrate.

The covering material and the extensible and contractible substrate are made of the same resin material, and thus, the extensible and contractible wiring board including the covering material can be obtained in one bonding step (e.g., a thermal pressure bonding step).

Such a covering material is provided at the extensible and contractible wiring board, and thus, the positions of the functional units (e.g., sensor units) can be fixed. Accordingly, the positions at which the sensors which are the functional units are provided are fixed on the same extensible and contractible substrate similarly to the extensible and contractible wiring board of the third embodiment. Thus, the relative position accuracy between the sensors is improved. Moreover, detection accuracy can be improved in some sensors.

The wirings included in the extensible and contractible wiring board are covered with the covering material, and thus, the wirings can be protected. Accordingly, disturbance noise can be further reduced.

Fifth Exemplary Embodiment

Next, still another embodiment of the extensible and contractible wiring board of the present invention will be described.

In the extensible and contractible wiring board of the present invention, an upper surface shield pattern sheet and a lower surface shield pattern sheet may be provided on an upper surface and a lower surface of an intermediate wiring portion, respectively, and upper and lower portions of the wirings of the intermediate wiring portions may be covered with shield patterns.

Hereinafter, an embodiment of such an extensible and contractible wiring board will be described.

A configuration of the extensible and contractible wiring board to be illustrated below is similar to the configuration of the extensible and contractible wiring board of the fourth exemplary embodiment except that the shield pattern sheets are further provided, and thus, portions different from the portions of the extensible and contractible wiring board of the fourth embodiment will be described.

Figure 11A:
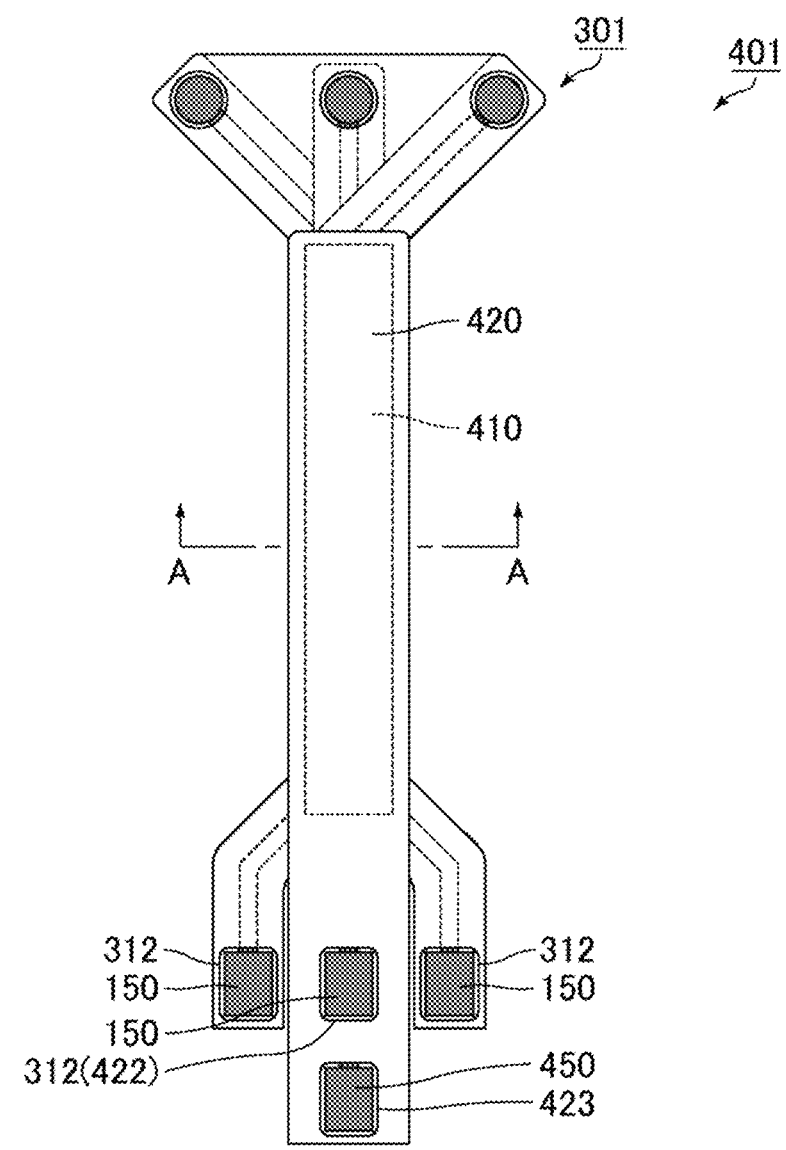
FIG. 11A is a top view schematically illustrating an extensible and contractible wiring board according to a fifth exemplary embodiment.
Figure 11B:
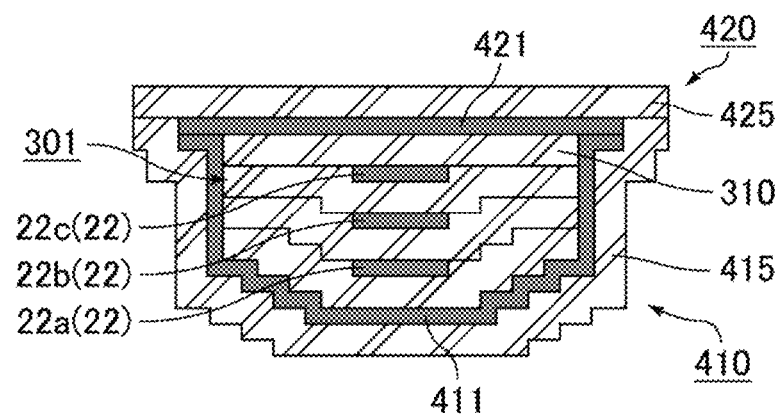
FIG. 11B is a sectional view taken along a line A-A of FIG. 11A.

FIG. 11A is a top view schematically illustrating an extensible and contractible wiring board according to a fifth exemplary embodiment, and FIG. 11B is a sectional view taken along a line A-A of FIG. 11A.

Figure 12:
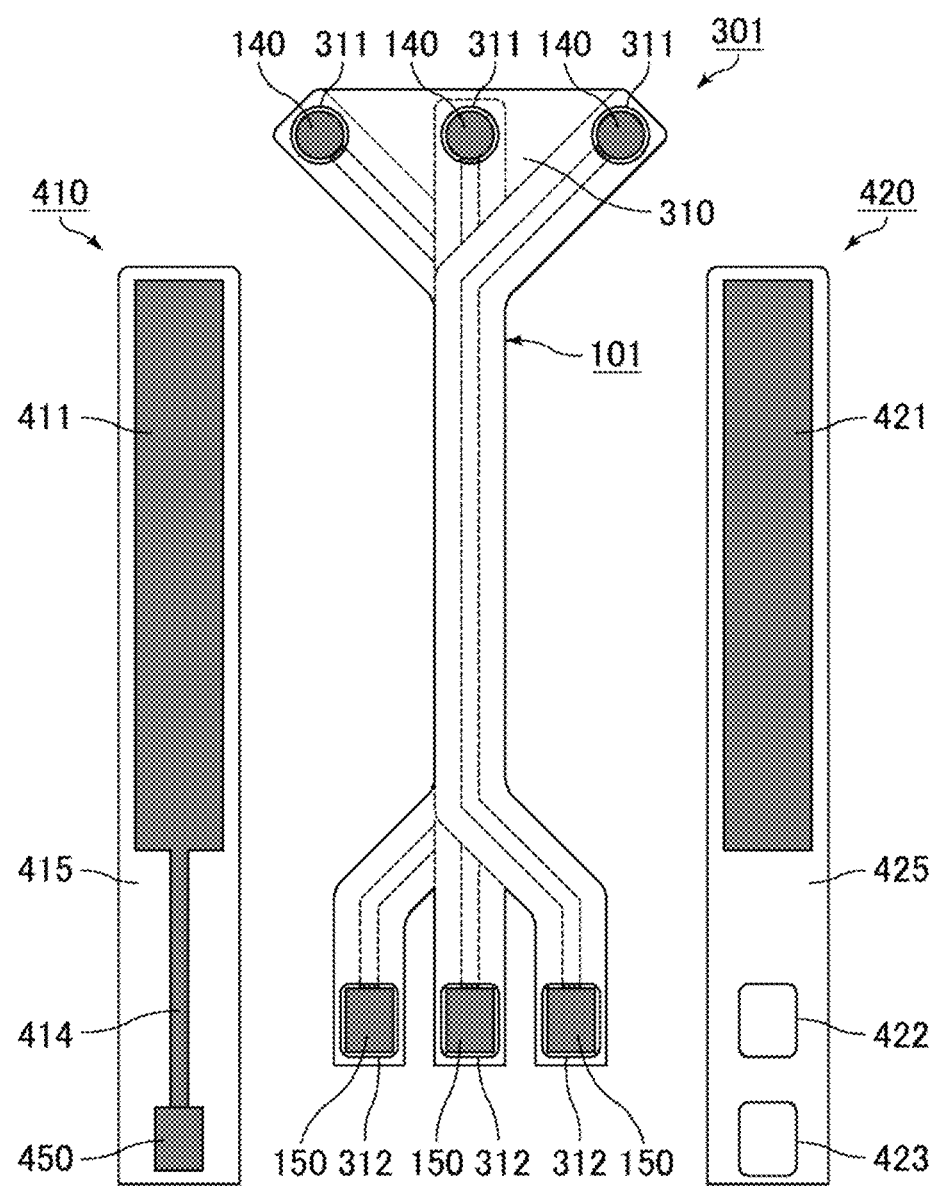
FIG. 12 is a top view schematically illustrating an extensible and contractible wiring board and a shield pattern sheet including the extensible and contractible wiring board according to the fifth exemplary embodiment.

FIG. 12 is a top view schematically illustrating an extensible and contractible wiring board and a shield pattern sheet including the extensible and contractible wiring board according to the fifth exemplary embodiment.

In an extensible and contractible wiring board 401 illustrated in FIGS. 11A and 11B, the extensible and contractible wiring board 301 of the fourth embodiment illustrated in FIG. 9 further includes the shield pattern sheets.

The extensible and contractible wiring board 301 of the fourth embodiment is illustrated in a center of FIG. 12, a lower surface shield pattern sheet 410 is illustrated on a left side, and an upper surface shield pattern sheet 420 is illustrated on a right side.

In the lower surface shield pattern sheet 410, a solid conductor pattern 411 is provided at an extensible and contractible substrate 415, and the solid conductor pattern 411 is connected to a connector 450 via a wiring 414.

In the upper surface shield pattern sheet 420, a solid conductor pattern 421 is provided at an extensible and contractible substrate 425. An opening 423 is provided at a position corresponding to the connector 450 of the lower surface shield pattern sheet 410. An opening 422 is provided at a position corresponding to the connector 150 of the extensible and contractible wiring board 301.

The solid conductor pattern 411 and the solid conductor pattern 421 are provided so as to cover upper and lower portions of the wirings 22 of the intermediate wiring portions 12 of the extensible and contractible wiring board 301.

FIG. 11B illustrates a positional relationship between the wirings 22 (the wiring 22a, the wiring 22b, and the wiring 22c) of the intermediate wiring portions 12 of the extensible and contractible wiring board 301 and the solid conductor pattern 411 and the solid conductor pattern 421.

When the lower surface shield pattern sheet 410, the extensible and contractible wiring board 301, and the upper surface shield pattern sheet 420 overlap and are thermally pressure-bonded, widths of the solid conductor pattern 411 and the solid conductor pattern 421 are set to be wider than a width of the intermediate wiring portion 12 of the extensible and contractible wiring board 301, and thus, the solid conductor pattern 411 and the solid conductor pattern 421 surround the wirings 22 of the intermediate wiring portions 12.

With such a configuration, disturbance noise (e.g., hum noise or electrostatic noise) can be prevented from being mixed at the intermediate wiring portions due to a shielding effect of the wirings being surrounded by the solid conductor patterns. Since the sheets are not additionally layered at the first end portions, flexibility and extension and contraction properties at the first end portions are maintained high.

Another aspect of the extensible and contractible wiring board of the present invention is an extensible and contractible wiring board including at least a first extensible and contractible wiring substrate formed by forming a wiring at an extensible and contractible substrate and a second extensible and contractible wiring substrate formed by forming a wiring at an extensible and contractible substrate. The first extensible and contractible wiring substrate and the second extensible and contractible wiring substrate are not electrically connected, each of the first extensible and contractible wiring substrate and the second extensible and contractible wiring substrate has a first end having a wiring and an intermediate wiring portion, the wiring of the first extensible and contractible wiring substrate and the wiring of the second extensible and contractible wiring substrate are not electrically connected, the first extensible and contractible wiring substrate and the second extensible and contractible wiring substrate are electrically independent extensible and contractible wiring substrates, the wirings do not overlap at the first ends of the first extensible and contractible wiring substrate and the second extensible and contractible wiring substrate in top view of the extensible and contractible wiring board, and the intermediate wiring portions of the first extensible and contractible wiring substrate and the second extensible and contractible wiring substrate overlap in top view of the extensible and contractible wiring board.

The extensible and contractible wiring board of the aforementioned aspect corresponds to the extensible and contractible wiring board having no functional unit among the extensible and contractible wiring boards of the exemplary embodiments described above.

In the extensible and contractible wiring board of the aforementioned aspect, since the intermediate wiring portions of the extensible and contractible wiring substrates overlap in top view of the extensible and contractible wiring board, an extensible and contractible wiring board with a small difference between noises at a plurality of provided wirings can also be achieved.

In the extensible and contractible wiring board of the aforementioned aspect, it is preferable that each of the first extensible and contractible wiring substrate and the second extensible and contractible wiring substrate has a second end which is an end portion opposite to the first end, and the second ends of the first extensible and contractible wiring substrate and the second extensible and contractible wiring substrate do not overlap in top view of the extensible and contractible wiring board.

An extensible and contractible wiring substrate was prepared by forming wirings made of a mixture of metal powder and an elastomer resin on a thermoplastic polyurethane resin as an extensible and contractible substrate. This extensible and contractible wiring was extended and contracted, and a relationship between an extension and contraction rate and a resistance change rate was measured.

Figure 13:
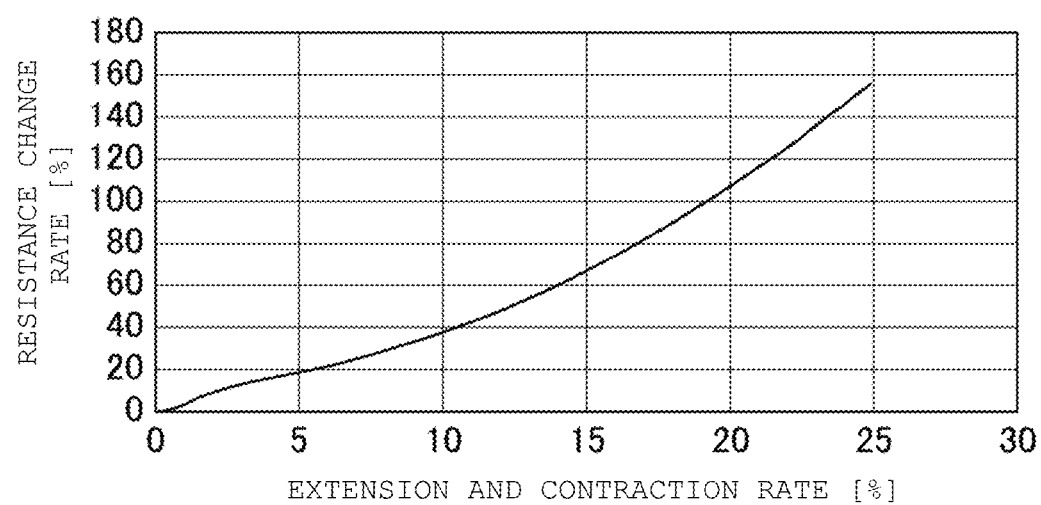
FIG. 13 is a graph showing a relationship between an extension and contraction rate and a resistance change rate of the extensible and contractible wiring substrate.

FIG. 13 is a graph showing a relationship between the extension and contraction rate and the resistance change rate of the extensible and contractible wiring substrate.

From the results shown in FIG. 13, it can be seen that the resistance change rate differs depending on the extension and contraction rate of the extensible and contractible wiring substrate. Accordingly, the degrees of extension and contraction applied to the wirings are set to be approximately equal, and thus, the degrees of noises caused at the plurality of wirings can be set to be approximately equal.

DESCRIPTION OF REFERENCE SYMBOLS 1, 101, 201, 301, 401: Extensible and contractible wiring board 10a, 110a, 210a: First extensible and contractible wiring substrate
10b, 110b, 210b: Second extensible and contractible wiring substrate
10c, 110c, 210c: Third extensible and contractible wiring substrate
11: First end portion
12, 12a, 12b, 12c: Intermediate wiring portion
13: Second end portion
21, 21a, 21b, 21c, 22, 22a, 22b, 22c, 22a", 22b", 22c", 23: Wiring
31, 31a, 31b, 31c, 32, 32a, 32b, 32c, 32", 33: Extensible and contractible substrate
40: Functional unit (heating element)
50, 50a, 50b, 50c, 150: Connector
61, 61a, 61b, 61c, 62, 62a, 62b, 62c, 63, 63a, 63b, 63c: Ground wiring
140, 140a, 140b, 140c: Functional unit (sensor)
310: Covering material
311,312: Opening of covering material
410: Lower surface shield pattern sheet
411, 421: Solid conductor pattern
414: Wiring of shield pattern sheet
415, 425: Extensible and contractible substrate of shield pattern sheet
420: Upper surface shield pattern sheet
422, 423: Opening of upper surface shield pattern sheet
450: Connector of shield pattern sheet

The invention claimed is:

1. A wiring board comprising:
a first wiring substrate including at an extensible and contractible substrate with a wiring thereon; and
a second wiring substrate having an extensible and contractible substrate with a wiring thereon,
wherein each of the first and second wiring substrates has a first end with a functional unit, a second end opposite the first end, and an intermediate wiring portion disposed between the first and second ends,
wherein the respective wirings and the functional units of the first and second wiring substrates are not electrically connected to each other,
wherein the respective wirings and the functional units do not overlap each other in a top view of the wiring board at the respective first ends of the first and second wiring substrates,
wherein the intermediate wiring portions of the first and second wiring substrates overlap each other in the top view of the wiring board,
wherein each of the first wiring substrate and the second wiring substrate and their respective first ends comprises a planar surface that extends in a direction parallel to each other.

2. The wiring board according to claim 1, wherein the first and second wiring substrates are electrically independent of each other.

3. The wiring board according to claim 1, wherein the second ends of the first and second wiring substrates do not overlap each other in the top view of the wiring board.

4. The wiring board according to claim 1, wherein the functional units of the first and second wiring substrates are heating elements.

5. The wiring board according to claim 4, further comprising ground wirings that are connected to the respective heating elements and that are disposed at the first ends, the intermediate wiring portions, and the second ends of the first and second wiring substrates, respectively.

6. The wiring board according to claim 5, wherein the ground wirings disposed at the intermediate wiring portions of the first and second wiring substrates do not overlap each other in the top view of the wiring board.

7. The wiring board according to claim 5, wherein the heating elements are LED elements, and the wiring board further includes connectors that are disposed at the respective second ends and are electrically connected to a conversion board that controls supply of power to the LED elements.

8. The wiring board according to claim 5, wherein the wiring board is configured for a visual function monitoring device.

9. The wiring board according to claim 1, wherein the respective wirings of the intermediate wiring portions of the first and second wiring substrates overlap each other in the top view of the wiring board.

10. The wiring board according to claim 1, wherein the extensible and contractible substrate of the first end of the first wiring substrate as a lowermost layer is positioned under the extensible and contractible substrate and the functional units of the first end of the second wiring substrate, and the extensible and contractible substrate of the first end of the second wiring substrate is fixed to the extensible and contractible substrate of the first end of the first wiring substrate as the lowermost layer.

11. The wiring board according to claim 1, further comprising:
a covering material that covers the wiring board,
wherein an opening extends in the covering material at a position of the functional unit relative to the top view of the wiring board.

12. The wiring board according to claim 1, further comprising:
an upper surface shield pattern sheet and a lower surface shield pattern sheet dispose on an upper surface and a lower surface of the intermediate wiring portion, respectively,
wherein upper and lower portions of the respective wirings of the intermediate wiring portions are covered with shield patterns, respectively.

13. The wiring board according to claim 1, wherein the intermediate wiring portions of the first and second wiring substrates each comprise a planar shape and directly overlap each other in the top view of the wiring board between the first and second ends of the first and second wiring substrates, respectively.

14. A wiring board comprising:
a first wiring substrate including a wiring on an extensible and contractible substrate; and
a second wiring substrate including a wiring on an extensible and contractible substrate,
wherein each of the first and second wiring substrates has a first end having a respective wiring and an intermediate wiring portion,
wherein the wiring of the first wiring substrate is not electrically connected to the wiring of the second wiring substrate,
wherein the respective wirings do not overlap each other at the first ends of the first and second wiring substrates in a top view of the wiring board,
wherein the intermediate wiring portions of the first and second wiring substrates overlap each other in the top view of the wiring board, and
wherein each of the first and second wiring substrates and their respective first ends comprises a planar surface that extends in a direction parallel to each other.

15. The wiring board according to claim 14, wherein the first and second wiring substrates are electrically independent from each other.

16. The wiring board according to claim 14,
wherein each of the first and second wiring substrates has a second end that is opposite to the first end with the intermediate wiring portion extending therebetween, and
wherein the respective second ends of the first and second wiring substrates do not overlap each other in the top view of the wiring board.

17. The wiring board according to claim 16, further comprising a plurality of functional units disposed on the respective first ends of the first and second wiring substrates.

18. The wiring board according to claim 17, wherein the functional units of the first and second wiring substrates are heating elements.

19. The wiring board according to claim 18, further comprising ground wirings that are connected to the respective heating elements and that are disposed at the first ends, the intermediate wiring portions, and the second ends of the first and second wiring substrates, respectively.

20. The wiring board according to claim 19, wherein the ground wirings disposed at the intermediate wiring portions of the first and second wiring substrates do not overlap each other in the top view of the wiring board.

21. The wiring board according to claim 19, wherein the heating elements are LED elements, and the wiring board further includes connectors that are disposed at the respective second ends and are electrically connected to a conversion board that controls supply of power to the LED elements.

22. The wiring board according to claim 16, wherein the intermediate wiring portions of the first and second wiring substrates each comprise a planar shape and directly overlap each other in the top view of the wiring board between the first and second ends of the first and second wiring substrates, respectively.

* * * * *